(12) United States Patent
Hansmann et al.

(10) Patent No.: US 9,885,693 B2
(45) Date of Patent: Feb. 6, 2018

(54) MEASURING DEVICE, REACTION CARRIER AND MEASURING METHOD

(71) Applicant: Dräger Safety AG & Co. KGaA, Lübeck (DE)

(72) Inventors: Hans-Ullrich Hansmann, Barnitz (DE); Philipp Rostalski, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 228 days.

(21) Appl. No.: 14/784,647

(22) PCT Filed: Apr. 15, 2014

(86) PCT No.: PCT/EP2014/001012
§ 371 (c)(1),
(2) Date: Oct. 15, 2015

(87) PCT Pub. No.: WO2014/170019
PCT Pub. Date: Oct. 23, 2014

(65) Prior Publication Data
US 2016/0061792 A1 Mar. 3, 2016

(30) Foreign Application Priority Data
Apr. 16, 2013 (DE) .................. 10 2013 006 542

(51) Int. Cl.
| | |
|---|---|
| *G01N 33/00* | (2006.01) |
| *G01N 31/22* | (2006.01) |
| *B01L 3/00* | (2006.01) |
| *G01N 21/13* | (2006.01) |
| *G01N 21/78* | (2006.01) |
| *G01F 1/708* | (2006.01) |

(Continued)

(52) U.S. Cl.
CPC .......... *G01N 31/223* (2013.01); *G01N 21/13* (2013.01); *G01N 21/783* (2013.01);
(Continued)

(58) Field of Classification Search
CPC ............. G01N 2021/115; G01N 21/13; G01N 21/783; G01N 31/223; G01N 33/0013
See application file for complete search history.

(56) References Cited

U.S. PATENT DOCUMENTS

| | | | |
|---|---|---|---|
| 4,123,227 A | 10/1978 | Heim et al. | |
| 5,069,220 A * | 12/1991 | Casparie | A61B 5/087 |
| | | | 600/532 |

(Continued)

FOREIGN PATENT DOCUMENTS

| | | |
|---|---|---|
| DE | 10 93 113 B | 11/1960 |
| DE | 26 28 790 B1 | 11/1977 |

(Continued)

OTHER PUBLICATIONS

"Dräger-Röhrchen & CMS-Handbuch 16, Auflage", Feb. 1, 2011 (Feb. 1, 2011), p. 2, 39, 70-105, 394, 398, XP55133367, Retrieved from the internet: URL:http://www.draeger.com/sites/assets/PublishingImages/segments/Industrie/Dokumente/roehrchen_handbuch_br_9092084_de.pdf,p. 72-p. 73, p. 74, p. 395.

*Primary Examiner* — Jennifer Wecker
(74) *Attorney, Agent, or Firm* — McGlew and Tuttle, P.C.

(57) ABSTRACT

A measuring system and device (12), a reaction carrier (14) and a measuring method for measuring a concentration of gaseous and/or aerosol components of a gas mixture are provided. The reaction carrier includes flow channels (42) and a coding that is detectable by a position sensor (36) to position the reaction carrier flow channels. At least one flow channel defines a reaction chamber (46) in which optically detectable reaction material (48) is provided. A position sensor detects a relative position of the reaction carrier. A conveying device (28) moves the reaction carrier relative to gas connections (22, 24) of a gas-inlet channel (16) and a gas-outlet channel (16, 18) between a measuring position with gas connections via a first flow channel for flushing the gas inlet channel and gas connections via a second flow (Continued)

channel defining a reaction chamber, for measuring the component of the gas mixture.

17 Claims, 10 Drawing Sheets

(51) Int. Cl.
  *G01N 21/27* (2006.01)
  *B01J 19/00* (2006.01)
  *G01N 21/11* (2006.01)

(52) U.S. Cl.
  CPC ....... *G01N 33/0013* (2013.01); *B01J 19/0093* (2013.01); *G01F 1/7086* (2013.01); *G01N 21/272* (2013.01); *G01N 2021/115* (2013.01)

(56) References Cited

U.S. PATENT DOCUMENTS

| | | | |
|---|---|---|---|
| 5,089,232 A * | 2/1992 | May | G01N 21/783 422/404 |
| 5,464,588 A | 11/1995 | Baether et al. | |
| 6,266,998 B1 | 7/2001 | Hackenberg | |
| 2008/0295617 A1* | 12/2008 | Trapp | G01N 30/20 73/863.72 |
| 2010/0015006 A1 | 1/2010 | Hsu | |
| 2013/0291622 A1* | 11/2013 | Heinemeyer | G01N 1/2294 73/23.2 |
| 2015/0192470 A1* | 7/2015 | Hansmann | G01N 21/05 356/408 |

FOREIGN PATENT DOCUMENTS

| | | | |
|---|---|---|---|
| DE | 39 02 402 C1 | 6/1990 | |
| DE | 43 45 151 A1 | 8/1994 | |
| DE | 44 15 866 C1 | 6/1995 | |
| DE | 10 2006 027 344 A1 | 1/2007 | |
| DE | 10 2012 014 503 A1 | 1/2014 | |
| DE | 10 2012 014 504 A1 | 1/2014 | |
| EP | 0 266 628 A2 | 5/1988 | |
| EP | 0 610 673 A1 | 8/1994 | |
| GB | 2 183 830 A | 6/1987 | |
| WO | WO 2014012977 A1 * | 1/2014 | ............ G01N 21/05 |

* cited by examiner

MEASURING DEVICE, REACTION CARRIER AND MEASURING METHOD

CROSS REFERENCE TO RELATED APPLICATIONS

This application is a United States National Phase Application of International Application PCT/EP2014/001012 filed Apr. 15, 2014 and claims the benefit of priority under 35 U.S.C. §119 of German Patent Application 10 2013 006 542.9 filed Apr. 16, 2013 the entire contents of which are incorporated herein by reference.

FIELD OF THE INVENTION

The present invention pertains to a measuring system and a measuring device for measuring a concentration of gaseous and/or aerosol components of a gas mixture for a reaction carrier, which has at least two flow channels, wherein at least one flow channel forms a reaction chamber with a reactant and the reactant reacts with at least one of the components to be measured in the gas mixture in an optically detectable manner. The present invention pertains, furthermore, to a reaction carrier for such a measuring device as well as to a measuring method for measuring a concentration of gaseous and/or aerosol components of a gas mixture.

BACKGROUND OF THE INVENTION

Gas detector tubes, which are filled with a reactant, which reacts with a chemical compound to be determined in an optically detectable reaction, are known from the state of the art. For example, a defined quantity of a gas mixture is pumped with a hand pump through the gas detector tube. A concentration of the chemical compound to be measured is subsequently determined by means of a discoloration of the reactant.

Moreover, so-called chip-based measuring systems are known, in which the reactant is arranged in reaction chambers on a reaction carrier, which can be inserted into a measuring device. The measuring device detects the reaction carrier and carries out a corresponding measuring method for measuring a concentration of the corresponding component of the gas mixture. For example, the reaction carrier has a plurality of reaction chambers, which may each be used for a measurement. A mechanical locking pin, which protrudes in unused reaction chambers, so that it can lock on the measuring device, is provided for each reaction chamber. The corresponding locking pin is pressed in during a measurement with a reaction chamber. Upon inserting the reaction carrier into the measuring device, the reaction carrier is always inserted into the measuring device until the first protruding locking pin mechanically locks in the measuring device and thus the first unused reaction chamber is always used for the respective measurement. After completion of the measurement, the reaction carrier is always completely ejected from the measuring device. An independent positioning of the reaction carrier in the measuring device in a desired relative position is not possible.

SUMMARY OF THE INVENTION

An object of the present invention is to provide an improved measuring device as well as a corresponding reaction carrier and an improved measuring method, which makes possible an increased flexibility in the measuring method and an accurate concentration determination.

A measuring device according to the present invention for measuring a concentration of gaseous and/or aerosol components of a gas mixture for a reaction carrier, which has at least two flow channels, wherein at least one flow channel forms a reaction chamber with a reactant, and the reactant reacts with at least one component to be measured in the gas mixture in an optically detectable manner, has a gas inlet channel and a gas outlet channel, which have each a gas port, wherein the gas ports are designed to establish a connection with one of the flow channels of the reaction carrier in order to make possible a flow of the gas mixture from the gas inlet channel through the flow channel to the gas outlet channel. The measuring device comprises, furthermore, a gas delivery device for delivering the gas mixture through the gas outlet channel, a reaction carrier delivery device for moving the reaction carrier in relation to the gas inlet channel and the gas outlet channel, and a position sensor for detecting a relative position of the reaction carrier and the gas ports, wherein the position sensor preferably detects a code at the reaction carrier, especially an optical code. The reaction carrier delivery device is designed to position the reaction carrier in a first position relative to the gas ports in a measuring process, for establishing a connection between the gas ports via a first flow channel for flushing the gas inlet channel, and to position it in a second position relative to the gas ports for establishing a connection between the gas ports via a second flow channel, which forms a reaction chamber, for measuring the at least one component in the gas mixture.

A complex movement of the reaction carrier within the measuring device during a measuring process is made possible in this way. In addition, the gas inlet channel can be flushed in the first relative position of the reaction carrier, as a result of which possible residual gas quantities from a previous measurement are flushed out in the gas inlet channel Advantageously, the measurement of the concentration can thus be carried out by means of the reaction chamber in the second relative position with increased accuracy.

In one embodiment, the reaction carrier delivery device comprises a motor, especially an electric servomotor, which makes possible a relative movement of the reaction carrier in at least two opposite directions. Any desired displacement between various relative positions of the reaction carrier in the measuring device is made possible in this way.

For example, the reaction carrier can be moved in and out of the measuring device via a single opening. Thus, a contamination of the interior of the measuring device via a second opening for moving in and out of the reaction carrier can be avoided.

In another embodiment, the measuring device comprises a storage device, which can store data of at least the previous measurement, especially data on the component to be measured in the gas mixture and the measured concentration, and wherein the measuring device preferably comprises an analysis device, which decides whether or not a flushing of the gas inlet channel will take place on the basis of the stored data of at least the previous measurement and of the component to be measured in the next measurement.

The measuring method can be adapted in this way as a function of the situation. Thus, the duration of the method can be reduced by unnecessary method steps not being carried out. For example, a flushing of the gas inlet channel is not necessary when the previous measurement concerned the same component to be measured in the gas mixture with identical or lower detection threshold and the component was not measured or was below the detection threshold.

The measuring device is preferably designed to read instructions stored on the reaction carrier or references (which are, for example, stored in a code or an information field-code/information field) to instructions stored in the measuring device for positioning the gas ports and/or activation elements and/or for carrying out the measuring method.

In another embodiment, the measuring device comprises a valve, which is arranged upstream of the gas inlet channel and which makes possible a gas flow through the gas inlet channel in a first position and prevents a gas flow through the gas inlet channel in a second position. The tightness of the gas inlet channel can be checked by closing the valve.

The gas inlet channel is preferably made of glass. In this way, a chemical reaction or a deposit of gas components on the wall of the gas inlet channel is prevented or reduced.

For detecting the optically detectable reaction, an optical sensor is designed, for example, as a digital camera, which has a correspondingly large recording field for detecting the at least one reaction chamber.

The recording field is preferably illuminated with broadband light, especially white light, and the optical sensor records a color image with a plurality of color channels. In order to make possible an optimal analysis for different color changes in different types of optically detectable reactions, the color channels may be analyzed each with different weightings.

Advantageously, the measuring device is portable and thus has a compact and lightweight design. The operating elements are preferably so large that an operation with safety gloves is possible.

In another aspect, the present invention pertains to a reaction carrier, wherein the reaction carrier is designed for a measuring device of the present application, with at least two flow channels, which extend each between two connection elements, wherein at least one flow channel forms a reaction chamber with a reactant, and the reactant reacts with at least one component to be measured in the gas mixture in an optically detectable manner. The connection elements are designed so as to establish a connection in a relative position, associated with the respective flow channel, of the reaction carrier and the measuring device to the gas ports of the measuring device in order to make possible a flow of the gas mixture from the gas inlet channel through the flow channel to the gas outlet channel. The reaction carrier comprises, further, a code, preferably an optical or electronic code, which is designed to be detected by the position sensor and to make possible an independent positioning of the reaction carrier in each of the relative positions associated with the flow channels.

Such a code makes possible a flexible independent positioning of the reaction carrier in various relative positions, as a result of which a flexible measuring method is made possible.

In another embodiment, the reaction carrier has a separate flow channel for flushing the gas inlet channel, wherein the flow channel does not form a reaction chamber with a reactant. This makes it possible to carry out a flushing process at any time by means of the flow channel without reaction chamber.

In another aspect, the present invention pertains to a measuring method for measuring a concentration of gaseous and/or aerosol components of a gas mixture with a reaction carrier, which has at least two flow channels, wherein at least one flow channel forms a reaction chamber with a reactant, and the reactant reacts with at least one component to be measured in the gas mixture in an optically detectable manner, and with a measuring device with a gas inlet channel and a gas outlet channel, which have each a gas port, preferably with a measuring device described in the present application, especially with a reaction carrier described in the present application. The measuring method comprises the method steps of positioning the reaction carrier in a first position relative to the gas ports of the measuring device and establishing a connection between the gas ports via a first flow channel; of delivering gas through the outlet channel, the first flow channel and the gas inlet channel for flushing the gas inlet channel; of positioning the reaction carrier in a second position relative to the gas ports of the measuring device and establishing a connection between the gas ports via a second flow channel, which has an unused reaction chamber; and of delivering a gas mixture to be measured through the gas outlet channel, the second flow channel and the gas inlet channel and determining the concentration of the at least one component by means of the optically detectable reaction in the reaction chamber of the second flow channel.

By the gas inlet channel being flushed in the first relative position of the reaction carrier, possible residual gas quantities from a previous measurement in the gas inlet channel are flushed out. In this way, the measurement of the concentration can be carried out by means of the reaction chamber in the second relative position with increased accuracy. In this context, an unused reaction chamber is a reaction chamber with which no measurement of a concentration was carried out.

According to a method variant, in each measurement by means of a reaction carrier, the reaction carrier is positioned in the same first relative position. This makes possible a simple process, because no special code that has to be able to code a code of changing first relative position has to be provided.

In this case, the connection is preferably established via a flow channel without a reaction chamber. Such a flow channel may also have, for example, a larger flow cross section than flow channels which form a reaction chamber. In this way, a larger volume flow can be transported, because the flow resistance is lowered and/or the flow cross section is increased.

Advantageously, the first relative position is in a direction of insertion of the reaction carrier into the measuring device in front of the second relative position. In this way, the reaction carrier has to be moved in only one direction for the positioning in the first and second relative positions.

According to an embodiment variant, the measuring method additionally comprises at least one of the following method steps: Deciding, in a certain measurement to be carried out, whether the steps of positioning in the first relative position and of flushing will be carried out, wherein the decision is made as a function of data of the previous measurement and/or data of the measurement to be carried out, especially data on the component to be measured in the gas mixture and of the measured concentration, stored in the measuring device; and/or establishing the connection between the gas ports in the first relative position via a flow channel with an unused reaction chamber, determining a concentration of the at least one component by means of the optically detectable reaction in the reaction chamber during the delivery of gas for flushing the gas inlet channel and deciding whether a measurement will be carried out at the second relative position with a second flow channel with unused reaction chamber as a function of the concentration determined during the flushing.

In this way, the measuring method can be accelerated, especially if the circumstances of the respective measurement allow a flushing process to become unnecessary. Should a reaction carrier be used, which has exclusively flow channels with reaction chamber, then a reliable measurement may also be carried out during the first-time use of the reaction carrier, wherein, if possible, only one flow channel with an unused reaction chamber is used.

Another method variant comprises the method steps of checking for leakage flows before the delivery of gas for flushing the gas inlet channel, wherein exclusively the gas port of the gas outlet channel is connected to a connection element of the flow channel, and gas is delivered through the gas outlet channel and the flow channel, wherein the gas flow through the gas outlet channel is measured for checking for leakage flows. In addition or as an alternative, the gas inlet channel may be closed upstream, preferably by means of a valve, and both gas ports of the gas outlet channel and of the gas inlet channel are connected to the associated connection elements of the flow channel, and gas may be delivered through the gas outlet channel, the flow channel and the gas inlet channel, wherein the gas flow through the gas outlet channel is measured for checking for leakage flows. In this way, the tightness of the measuring system, consisting of the measuring device and the reaction carrier, can be checked. Thus, an undesired suction of gas via leakage points and a corresponding distortion of the measurement result is prevented. A corresponding warning can be sent to the user, whereupon the tightness of the reaction carrier and/or of the measuring device can be checked.

In another method variant, a volume flow through the gas outlet channel is determined and a delivery time of the flushing process is calculated. Thus, for example, the delivery time of the flushing process may be designed to flush a multiple, for example, double, the volume of the gas inlet channel.

Another aspect of the present invention pertains to a measuring system with a measuring device described in the present application and with a reaction carrier described in the present application, especially suitable for carrying out a measuring method described in the present application.

The above-described embodiments may be combined with one another and with the aspects described above as desired in order to obtain the advantages according to the present invention. Preferred combinations of the above-described embodiments are described as examples below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
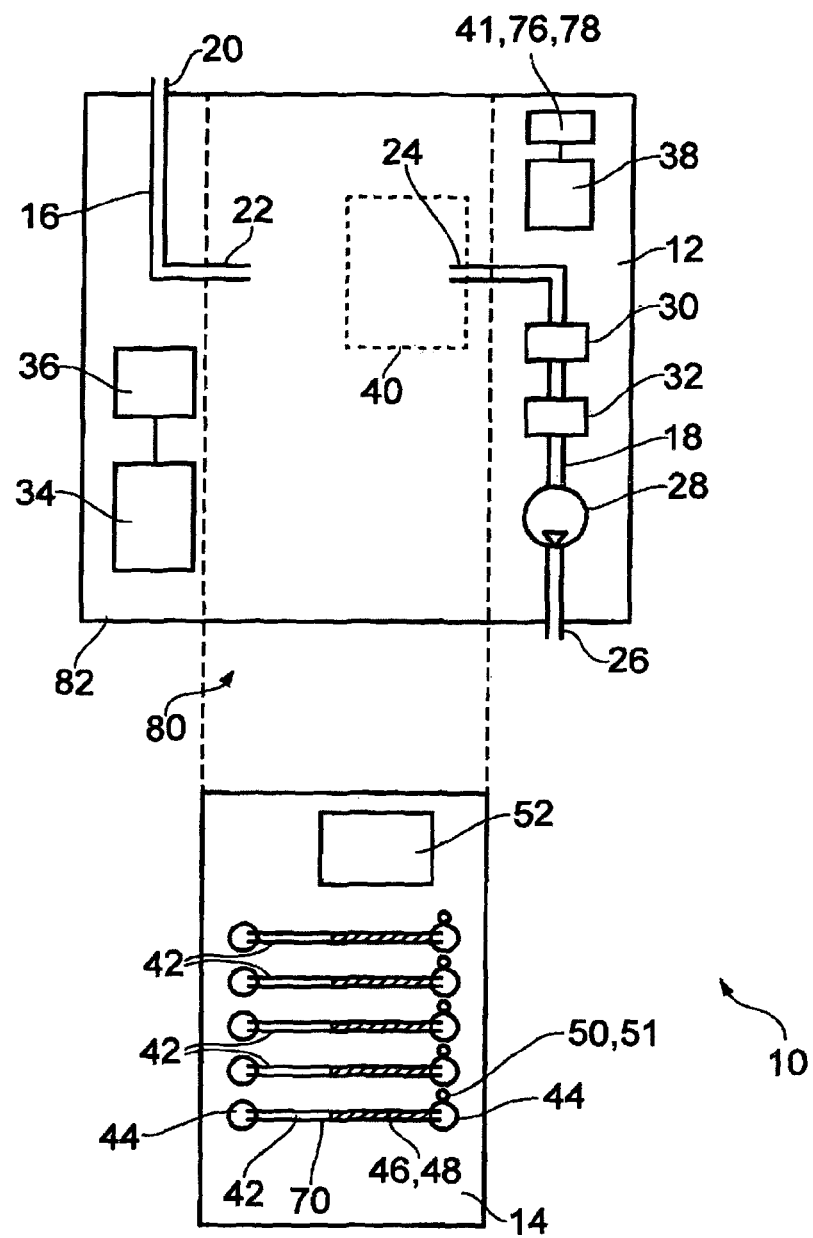
FIG. 1 is a schematic view of a first embodiment of a measuring system according to the present invention with a measuring device according to the present invention and with a reaction carrier according to the present invention.

FIG. 1 illustrates a first embodiment of the present invention. A gas measuring system, which is hereinafter also called measuring system 10, is used for measuring and detecting the concentration of gaseous or aerosol components. An exchangeable reaction carrier 14, which is also called reaction carrier unit, is manually inserted by a user in a measuring device 12, which is also called gas measuring arrangement or otherwise gas measuring system. Here, the measuring system 10 or the measuring device 12 is a small, portable device, which can be used under mobile conditions and is provided with a battery as an energy supply.

A gas delivery device 28, which is embodied by a pump designed as a suction pump, is arranged on a housing of the measuring device 12. The housing forms, in addition, a mount, especially a sliding mount, for the displaceable reaction carrier 14. The reaction carrier can be moved within the housing of the measuring device by means of a reaction carrier delivery device 34 with a motor, e.g., an electric motor designed as a servomotor and a gear mechanism, especially a driving roll, which is rotatable by the servomotor, because there is a mechanical contact or a connection between the driving roll and the reaction carrier.

The measuring system 10 comprises the measuring device 12 and at least one reaction carrier 14. The measuring device 12 has a gas inlet channel 16 and a gas outlet channel 18. The gas inlet channel 16 extends from a gas mixture inflow opening 20 to a first gas port 22. The gas outlet channel 18 extends from a second gas port 24 to a gas mixture outflow opening 26. Furthermore, the gas delivery device 28, for example, a suction pump, is provided in the gas outlet channel 18 for the delivery of a gas or gas mixture through the gas outlet channel 18.

The gas inlet channel 16 is made of glass, as a result of which a chemical reaction or a deposit of gas components on the wall of the gas inlet channel is prevented or reduced.

A flow sensor 30, which is designed as a mass flow sensor in the embodiment being shown, makes possible the measurement of a gas flowing through the gas outlet channel 18. Both devices, which measure the flow or the mass flow directly, as well as those which detect other measured values and determine the flow or mass flow by means of these measured values, may be used as flow or mass flow sensors.

Furthermore, a buffer 32, which makes possible a uniform gas flow through the gas outlet channel 18, is arranged in the gas outlet channel 18.

The measuring device 12 comprises, moreover, a reaction carrier delivery device 34, which makes possible a movement of the reaction carrier 14 in relation to the gas inlet channel 16 and to the gas outlet channel 18.

A position sensor 36 is used for detecting a relative position of the reaction carrier 14 and the gas ports 22, 24.

An optical sensor for detecting an optically detectable reaction is provided in the form of a digital camera 38 and makes possible a recording of the recording field 40 shown in FIG. 1 by the dotted rectangle.

A central control unit 41 is provided, which can process the data detected by the optical sensor and controls the measuring method.

The reaction carrier 14 has a plurality of flow channels 42, which extend between two connection elements 44 each. In the embodiment being shown, each of the flow channels 42 forms a reaction chamber 46, which is filled with a reactant 48. The reactant 48 is a chemical compound, which is designed to react with a gas to be measured and/or an aerosol component in a gas mixture in an optically detectable manner. This is, for example, a colorimetric reaction.

In the embodiment being shown, the flow channels 42 are each filled with the reactant 48 on their right side. A different gas treatment element, for example, a desiccant, is provided on the left side of the flow channels 42.

A display pin 50, which forms a code 51, which is detected by the position sensor 36 and makes possible an independent positioning of the reaction carrier 14 in relative positions associated with each of the flow channels 42, is associated with each flow channel 42. A different type of code 51, for example, an electric, electronic or magnetic code may also be provided, which can be detected by a corresponding position sensor 36. However, at least additionally one optical code 51 is preferably provided, so that a user of the measuring system 10 can determine at a glance by looking at the reaction carrier 14 whether the reaction carrier still has unused reaction chambers.

The reaction carrier 14 has, furthermore, an information field 52, on which information is stored. In the embodiment being shown, the information field 52 is designed as an optical information field, on which information is stored, which can be read by the digital camera 38. As an alternative, the information field 52 may be provided as an electronic memory for information and be designed, for example, as an RFID chip or SROM chip, which may be read and/or written in a wireless manner or via electric contacts.

The recording field of the digital camera 38 is designed in the embodiment being shown, such that the reaction chambers 46, the display pins 50 and the information field 52 are detected by the digital camera 38 each in at least one relative position of the reaction carrier 14 in the measuring device 12. In this way, the digital camera 38 can be used, on the one hand, for the detection of the optically detectable reaction of the reactant 48 in the reaction chambers 46 of the reaction carrier 14 and, on the other hand, for reading the information in the information field 52 and as a position sensor 36 for detecting the relative position of the reaction carrier and the gas ports 22, 24. However, it is also possible that the position sensor 36 and a reading device for reading the information field 52 are designed as one or two separate devices.

Figure 2:
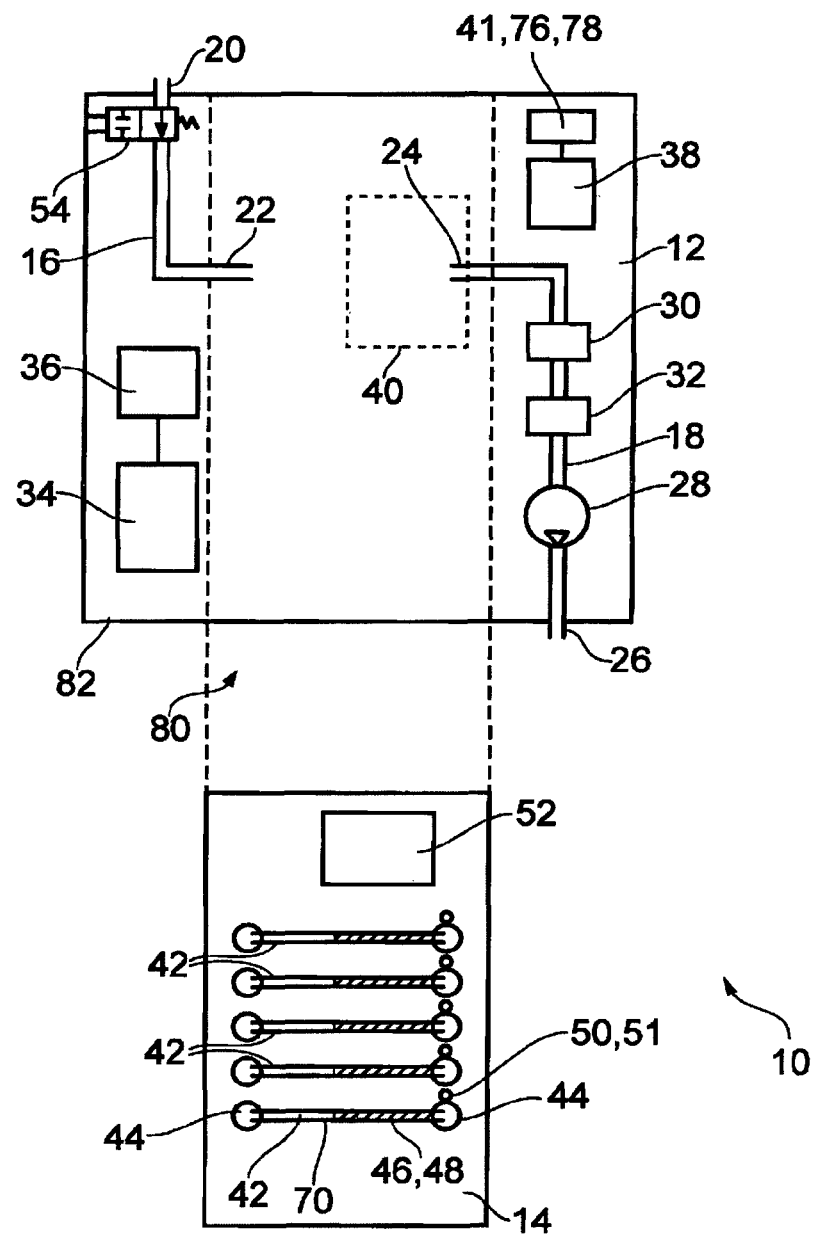
FIG. 2 is a schematic view of a second embodiment of a measuring system according to the present invention with a measuring device according to the present invention and with a reaction carrier according to the present invention.

FIG. 2 shows a second embodiment of the measuring device 12, which differs from the previous embodiment only by a valve 54. The valve 54 is arranged at the gas mixture inflow opening 20 upstream of the gas inlet channel 16. The valve makes possible, in its first position shown, a gas flow through the gas inlet channel 16 and prevents a gas flow through the gas inlet channel 16 in a second position. In the embodiment being shown, the valve 54 is designed as a 2/2-way valve.

Figure 3:
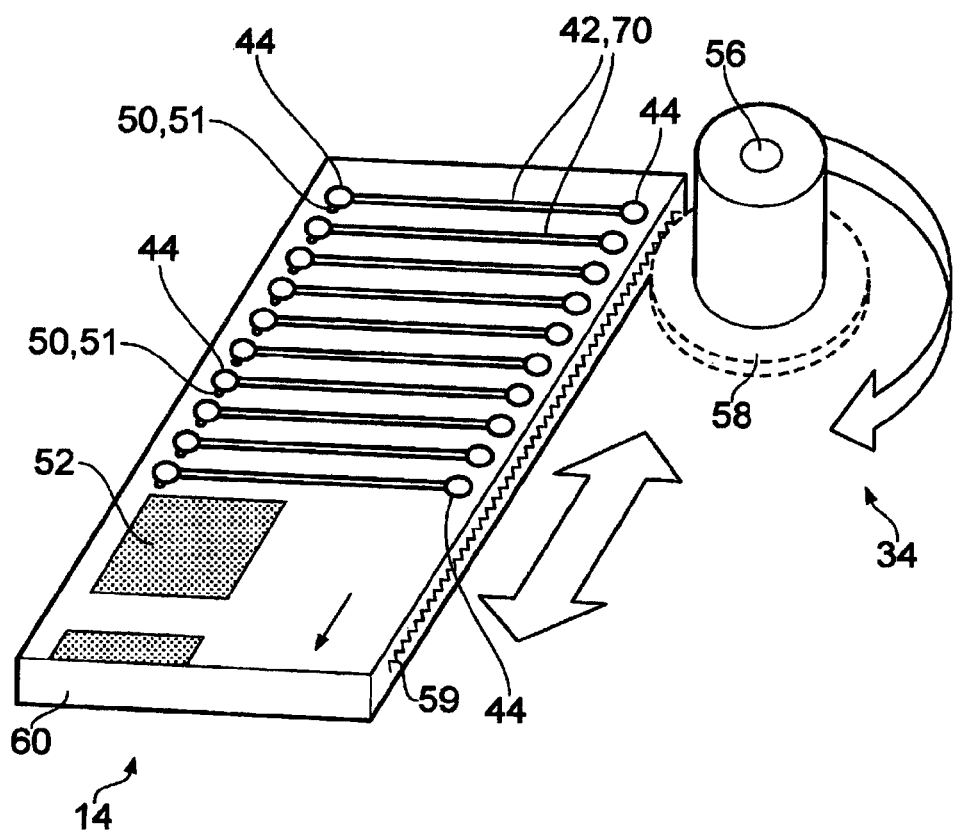
FIG. 3 is a detail view of a reaction carrier with of a reaction carrier delivery device.

FIG. 3 shows a perspective detail view of the reaction carrier 14 and of the reaction carrier delivery device 34 of the measuring device 12. The reaction carrier delivery device 34 comprises a servomotor 56 and a gear mechanism 58. The gear mechanism 58 comprises, for example, a gear wheel, which meshes with corresponding teeth 59 at the reaction carrier 14. The teeth 59 are formed on a housing 60 of the reaction carrier 14.

The reaction carrier delivery device 34 makes possible a relative movement of the reaction carrier 14 in two opposite directions, as a result of which a desired positioning of the reaction carrier 14 in the measuring device 12 is made possible. Preferably, the reaction carrier 14 is moved into and removed from the measuring device 12 through a single feed opening in a housing of the measuring device 12.

The reaction carrier 14 comprises a housing 60, which is transparent to light. Ten tubes designed as glass tubes are arranged on a top side of the housing 60, which top side is shown in FIG. 3, so that the tubes define a flow channel 42 and an identical reactant is arranged within this flow channel 42 or the tubes in the ten glass tubes. At an end of the glass tubes shown on the right in FIG. 3, these tubes have an inflow opening, and they have an outflow opening at an end of the glass tubes, which is shown on the left in FIG. 3. The inflow and outflow openings are sealed in a fluid-tight manner by a seal 64, for example, a glass seal. It is consequently ensured that the reactant within the glass tubes will not undergo any change in color on the reactant or the reactants because of an unintended and uncontrolled admission of the reactant with gaseous and/or aerosol components before the gas mixture passes through the tubes by means of a gas delivery device 28, for example, a suction pump. The reactant is used, for example, to detect acetone, so that a change occurs in the color of the reactant when passing through a gas mixture containing acetone. A display pin 50 each is arranged in the area of the outflow openings. A display pin 50 is thus associated with each of the ten glass tubes. Furthermore, an optical code is also present as a matrix code or matrix bar code on the top side of the housing 60.

The inflow and outflow openings together with their seal 64 form the connection elements 44 of the flow channels 42.

The gas ports 22 and 24 of the gas inlet channel 16 and of the gas outlet channel 18 as well as the corresponding connection elements 44 of the reaction carrier 14 are described below on the basis of FIGS. 4 through 7.

Figure 4:
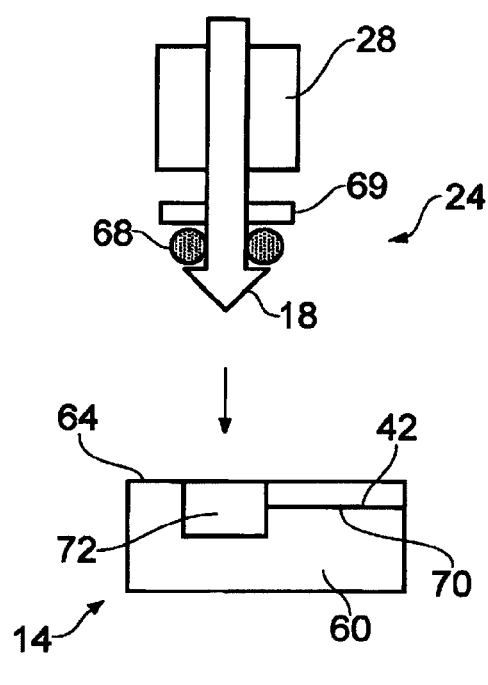
FIG. 4 is a detail view of a first embodiment of the gas port and of the connection element of the reaction carrier in a first position.
Figure 5:
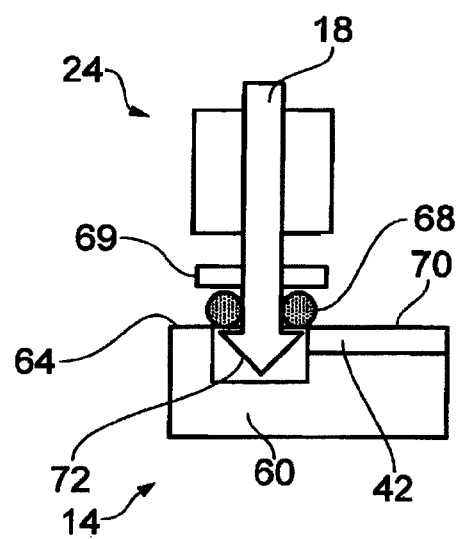
FIG. 5 is a detail view of a first embodiment of the gas port and of the connection element of the reaction carrier in a second position.

A first embodiment is described in FIGS. 4 and 5 as an example of the gas port 24 of the gas outlet channel 18. A gas connection piece of the gas outlet channel 18 and a seal 68 is arranged at the gas delivery device 28. An elastic sealing ring, for example, a rubber sealing ring, lies on the underside of a support ring 69 enclosing the gas connection piece and is fastened to the support ring 69, and the sealing ring forms the seal 68. The support ring 69 has, in addition, an expansion as a display pin-moving element (not shown) at right angles to the drawing plane of FIGS. 4 and 5. FIG. 4 shows a first position of the gas port 24 and FIG. 5 shows a second position. No gas can be drawn in from the gas delivery device 28 through the gas tube of the flow channel 42 and the seal is still closed in the first position according to FIG. 4. During a motion of the gas port 24, the seal is first broken up or pierced by the gas connection piece and the sealing ring is then placed on the housing 60 and the glass tube on the outside, on the top side, so that the opening inserted into the seal is completely sealed. Moreover, the seal at the corresponding inflow opening of the glass tube is pierced by an additional connection piece of the other gas port 22 (not shown) and opened, so that the gas mixture can flow into the glass tube through the inflow opening. The gas delivery device 28 is subsequently activated and consequently the gas mixture is drawn in through the inflow opening, then sent around the reactant and the gas mixture is admitted to the reactant, and the gas mixture is subsequently delivered again into the surrounding area through the outflow opening, the gas connection piece and the gas delivery device 28.

Figure 6:
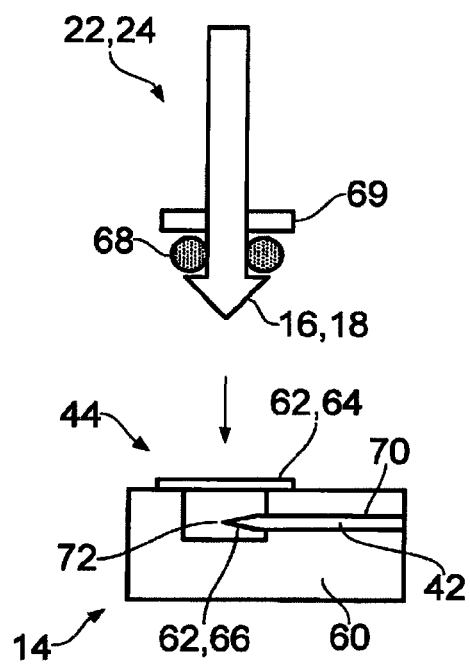
FIG. 6 is a detail view of a second embodiment of the gas port and of the connection element of the reaction carrier in a first position.
Figure 7:
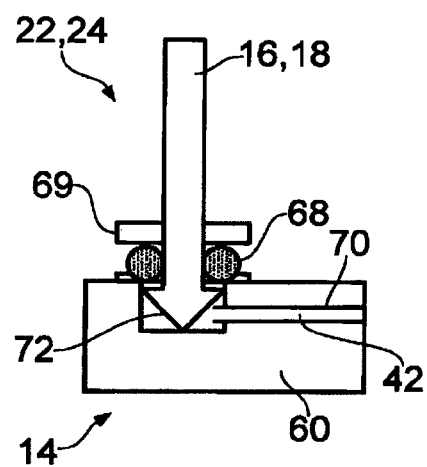
FIG. 7 is a detail view of a second embodiment of the gas port and of the connection element of the reaction carrier in a second position.

An alternative embodiment of the gas ports 22, 24 and connection elements 44 is shown in FIGS. 6 and 7. The connection elements 44 of the reaction carrier 14 comprise a sealing device 62 with a first seal 64 and a second seal 66, which prevent a penetration of gas into the flow channel 42. The flow channel 42 is formed by a tube 70, by a glass tube in the embodiment being shown, which is embedded into the housing 60 of the reaction carrier 14. The glass tube ends in a recess 72 in the housing 60. The recess 72 in the housing 60 is closed by the first seal 64. The first seal 64 is formed, for example, by a small glass plate or a film. The second seal 66 is formed by a closed end of the glass tube. The closed end of the glass tube of the flow channel 42 extends freely into the recess 72 in the housing 60.

The gas ports 22, 24 are formed at the end of the gas inlet channel 16 or at the beginning of the gas outlet channel 18. The gas port 22, 24 comprises a seal 68 and a gas connection piece. FIG. 6 shows the gas port 22, 24 in a starting position, in which the gas port 22, 24 is separated from the connection element 44 of the reaction carrier 14. The gas port 22, 24 may be lowered in the direction of the reaction carrier 14 or, as an alternative, the reaction carrier 14 may be moved in the direction of the gas port. During the lowering of the gas port 22, 24, the lower end of the gas connection piece strikes the first seal 64 and pierces same. The seal 68 of the gas port 22, 24 then comes into contact with the housing 60 of the reaction carrier 14 and forms a gas-tight seal of the recesses 72 of the connection element 44.

Upon further lowering of the gas port 22, 24, the gas connection piece breaks off the closed end of the glass tube 70 of the flow channel 42 and in this way opens the second seal 66 of the connection element 44. FIG. 7 shows the end position of the gas port 22, 24, in which the connection between the gas port 22, 24 and the connection element 44 of the flow channel 42 is established.

As an alternative, it is possible that the first seal 64 has, for example, a flexible design, so that a piercing of the first seal 64 only occurs when the seal 68 of the gas port 22, 24 is already in contact with the housing 60 of the reaction carrier 14 in a sealing manner. It is also possible that the seal 68 is designed such that it first comes into contact with the housing 60 of the reaction carrier 14 upon lowering of the gas port 22, 24 to the seal of the recess 72. Furthermore, it is also possible that only one of the seals 64 or 66 of the sealing device 62 is provided at the connection elements 44 of the reaction carrier 14.

Figure 8:
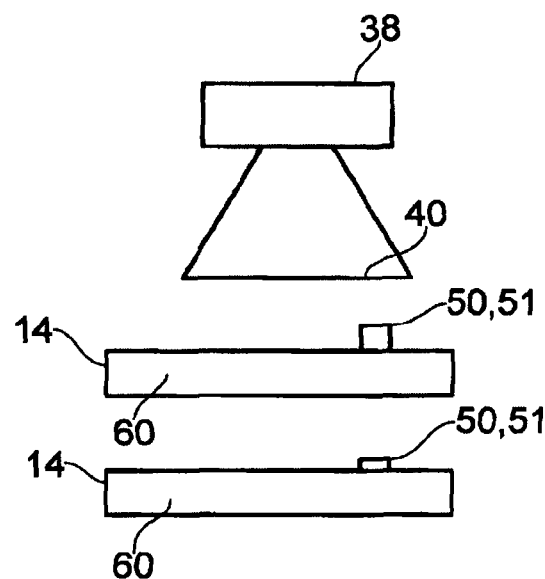
FIG. 8 is a composite side view of the digital camera and the reaction carrier with a display pin in a first position and the reaction carrier with the display pin in a second position.
Figure 9:
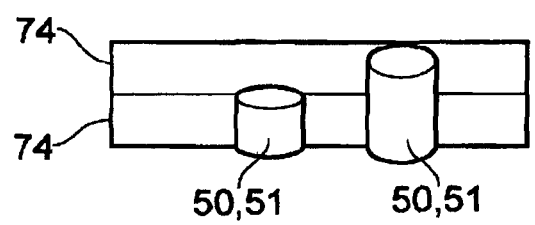
FIG. 9 is a perspective view of the display pin in the first position and display pin in the second position.

The code 51 of the reaction carrier 14 for the independent positioning of the reaction carrier 14 in a plurality of different relative positions in the measuring device 12 is described below on the basis of FIGS. 8 and 9.

The position sensor 36 for detecting the relative position of the reaction carrier 14 and the gas ports 22, 24 is embodied by the digital camera 38 in the embodiment being shown together with the optical sensor for detecting the optically detectable reaction of the reactant 48. In this way, no separate component is needed for the function of the position sensor. However, it is also possible that a non-optical position sensor, for example, an electric or magnetic position sensor, is provided, which can detect a corresponding code 51 of the reaction carrier 14.

The detection of the position of the reaction carrier 14 likewise takes place in a simple manner by means of the digital camera, because the analysis device has a corresponding optical software, by means of which the position of the reaction carrier 14 can be determined based on the data detected by the digital camera. The gas port 22, 24 is subsequently moved downwards, so that consequently the seal can be pierced by the gas connection piece and the gas mixture can be drawn in through the outflow opening. The display pin 50 is additionally moved by an expansion or display pin-moving element of the support ring (not shown) from a first position according to the upper reaction carrier 14 in FIG. 8 into a second position according to the lower reaction carrier 14 in FIG. 8. In the first position of the display pin 50, this pin projects farther out of the housing 60 of the reaction carrier than in the second position. The position of the display pin 50 may also be detected with the digital camera, and the display pin has a different color, for example, orange, than the rest of the reaction carrier 14, for example, the housing 60 is colored at least partially blue. The digital camera 38 has two separate ROIs (regions of interest), i.e., partial areas 74 of the recording field 40 of the digital camera 38, so that the color orange appears in the upper partial area 74 in FIG. 9 in the first position and no color or a substantially smaller quantity of the color of the display pin 50 appears on the upper partial area 74 in the second position. Consequently, it is possible to detect by the optical analysis software of the analysis device of the central control unit 41 whether a display pin 50 is located in the first or second position. Based on this detection of the first or second position of the display pin 50, the reaction carrier delivery unit 34 is moved, furthermore, independently and automatically by the servomotor 56 into such a position that the first, up to now unused glass tube, through which no gas has been passed up to now, lies with the outflow opening above the gas connection piece of the gas port 22, 24, and it is only thereafter that the gas port 22, 24, especially the suction pump and the gas connection piece, are moved downwards corresponding to FIGS. 4 and 5.

In the embodiment being shown, the display pin 50 is always arranged adjacent to the connection elements 44 at the edge of the reaction carrier 14. The display pin 50 thus lies in the edge area of the recording field 40 of the digital camera 38 and is thus detected by the digital camera 38 obliquely at an angle, as a result of which the height of the display pin can be detected.

In this way, the digital camera 38 or the optical analysis software can detect a position of a display pin 50, on the one hand, and thus approach any desired relative position of the reaction carrier 14 in the measuring device 12 via the reaction carrier delivery device 34. On the other hand, the information on whether or not the corresponding flow channel 42 has already been used can be read based on the height of the display pin 50.

Instead of an optical code 51, for example, an electric or magnetic code 51 may also be provided, which can be embodied, for example, by means of an electrically conductive field on the surface of the housing 60.

Figure 10:
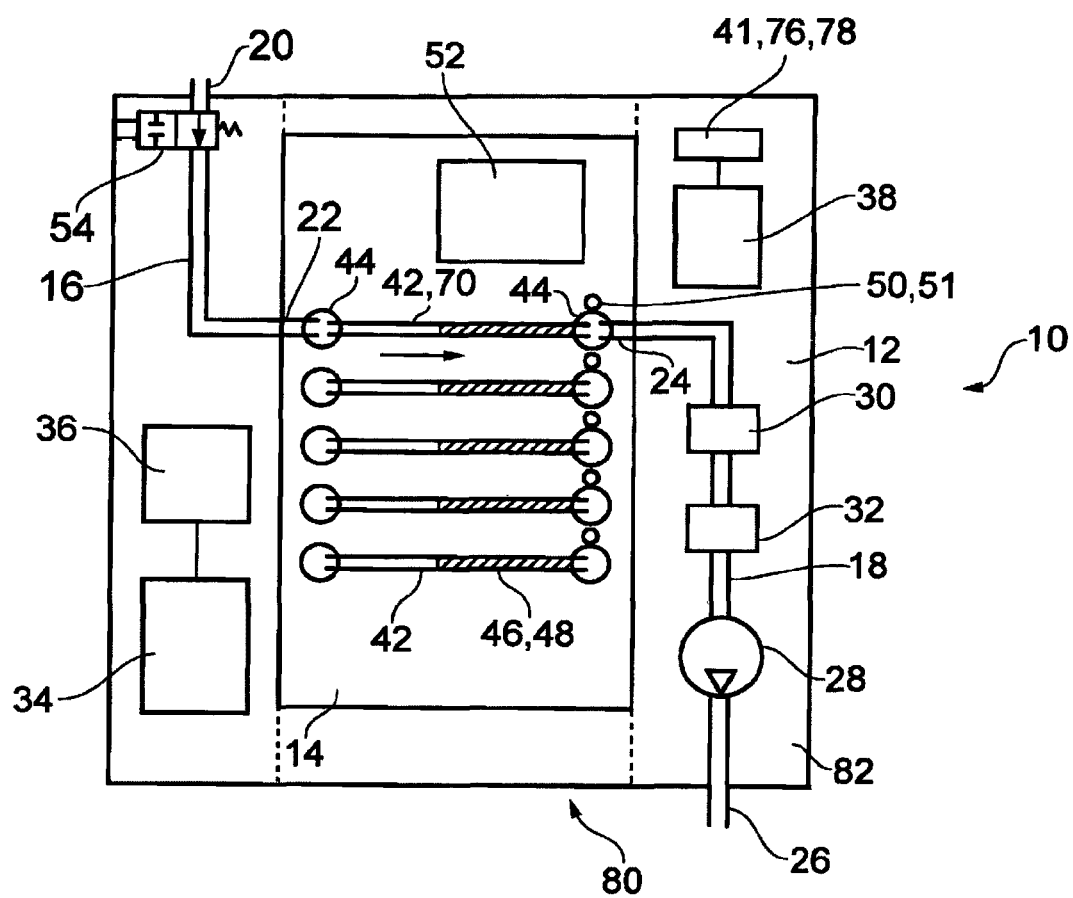
FIG. 10 is a schematic view of a measuring system according to the second embodiment, wherein the reaction carrier is located in a first relative position in the measuring device.
Figure 11:
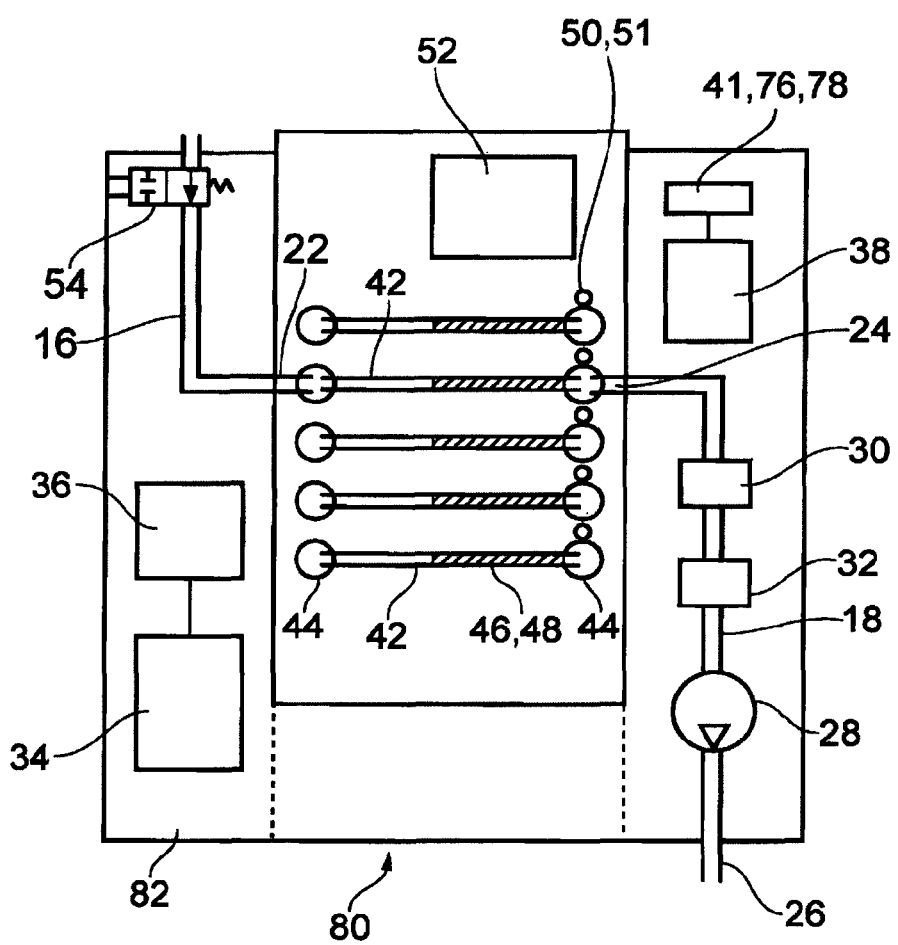
FIG. 11 is a schematic view of the measuring system according to the second embodiment, wherein the reaction carrier is located in a second relative position in the measuring device.

An embodiment of the measuring system 10 with the measuring device 12 according to FIG. 2 and a first embodiment of the reaction carrier 14 is shown in FIGS. 10 and 11. The reaction carrier 14 comprises a plurality of flow channels 42, wherein five flow channels each are provided in the embodiment being shown. The flow channels 42 are each designed identically and extend between the respective connection elements 44. The flow channels 42 are designed as glass tubes 70, in which a reaction chamber 46 is formed, which is filled with a reactant 48.

A measuring method is described below with reference to FIGS. 10 and 11.

The reaction carrier 14 is inserted into an insertion opening 80 in a housing 82 of the measuring device 12. The reaction carrier 14 is inserted manually into the insertion opening, detected by the reaction carrier delivery device 34 and transported forwards in the direction of insertion.

During the transporting of the reaction carrier 14, the information field 52 of the reaction carrier 14 passes through the recording field 40 of the digital camera 38, wherein the information on the information field 52 is detected by the digital camera 38 and can be analyzed in an analysis device of the central control unit 41. It is also possible that the reaction carrier is positioned in a reading position, in which a reading of the information field 52 is made possible. In the embodiment shown, the information on the information field 52 is stored optically and can thus be read by the digital camera 38 in a simple manner. It is also possible, as an alternative, that an electronic information field 52 is provided, which is designed, for example, as an active or passive RFID chip or SRAM chip and can be read in a wireless manner or via electric contacts. The electric contacts are preferably established via data lines to the inflow and outflow openings of the flow channels 42 and gas connection pieces consisting of a current-conducting material, so that a current and data connection is established between the SRAM chip and a corresponding reading device, while the gas connection pieces are located in the inflow and outflow openings.

The information of the reaction carrier 14 contained on the information field 52, and especially in relation to the component to be measured in the gas mixture and a corresponding concentration area is read in a first method step.

It is then decided whether a flushing process for flushing the gas inlet channel 16 shall be carried out in the measurement to be carried out. For this, for example, the data of the measurement to be carried out and of the previous measurement are taken into account, especially data on the component to be measured in the gas mixture and the previously measured component in the gas mixture and its concentration. Thus, a flushing process can be omitted, for example, in consecutive measurements of the same types of components, when the component was not detected in the previous measurement or the concentration was below the concentration threshold of the concentration range of the measurement to be carried out now. By omitting the flushing process, the measurement can be carried out more quickly. Furthermore, it is possible to carry out an immediate measurement when using a new reaction carrier 14 without already used flow channels 42, so that only one unused flow channel 42 is needed for the measurement.

When an analysis device 76 of the central control unit 41 has decided to carry out a flushing of the gas inlet channel, then the reaction carrier 14 is positioned in a first relative position, in which a selected flow channel 42 is used for flushing the gas inlet channel 16. Preferably, the selected flow channel 42 is an already used flow channel 42. This may be, for example, the first flow channel in the direction of insertion or the flow channel 42 last used on this reaction carrier 14.

In the case in which the reaction carrier 14 does not have an already used reaction chamber 46, the connection can be established between the gas ports 22 and 24 in the first relative position of the reaction carrier 14 via a flow channel 42 with an unused reaction chamber 46. During the delivery of gas for flushing the gas inlet channel 16, a concentration of the at least one component to be measured is determined by means of the digital camera 38 by means of the optically detectable reaction in the reaction chamber 46. In a subsequent method step, it is decided whether a measurement shall be carried out at the second relative position with a second flow channel with unused reaction chamber. The decision is made, for example, on the basis of the concentration determined during the flushing as well as, for example, information of a previous measurement and the results thereof. If these results essentially allow ruling out a possible multiple measurement, the measurement with the second flow channel 42 in the second relative position of the reaction carrier 14 can be omitted, as a result of which the second flow channel with the unused reaction chamber is available for another measurement. The measuring device thus outputs the concentration measured during the flushing of the gas inlet channel as a measurement result.

In the case in which the reaction carrier 14 has at least one already used reaction chamber 46 or a flow channel 42 without reaction chamber 46 intended for flushing, the reaction carrier 14 is positioned in a first position relative to the gas ports 22, 24 of the measuring device 12, which corresponds to the flow channel intended for flushing, which is hereinafter called first flow channel 42. In the first relative position, a connection is established between the gas ports 22 and 24 via the first flow channel by lowering the gas ports 22, 24. In the embodiment being shown, this first flow channel 42 is the flow channel 42 foremost in the insertion direction. However, a different flow channel 42 may, in principle, also be selected to be used as the first flow channel 42 corresponding to the first relative position.

The gas delivery device 28 delivers gas through the gas outlet channel 18, the first flow channel 42 and the gas inlet channel 16 for flushing the gas inlet channel. In this way, gas remaining from a previous measurement in the gas inlet channel 16 is flushed from the gas inlet channel 16. The duration of the flushing of the gas inlet channel may be fixed at a predetermined value, or a defined volume of gas, which corresponds, for example, to a defined multiple of the volume of the gas inlet channel 16, by means of the flow sensor 30.

The reaction carrier 14 is subsequently positioned in a second position relative to the gas ports 22, 24 of the measuring device 12, wherein a flow channel 42 is selected, which has an unused reaction chamber 46. A connection is established between the gas ports 22, 24 via the second flow channel 42 and the gas delivery device 28 delivers a gas mixture to be measured through the outlet channel 18, the second flow channel 42 and the gas inlet channel 16, wherein the digital camera 38 detects a possible optically detectable reaction in the reaction chamber 46 and a concentration of the component to be determined in the gas mixture is determined by means of the course over time or the degree of discoloration of the optically detectable reaction. If the component to be determined in the gas mixture is not contained in the gas mixture or is present in a concentration below a detection threshold of the concentration range of the present reaction carrier, then no optically detectable reaction is found in the reaction chamber. A corresponding result of the measurement is displayed, for example, optically or acoustically by the measuring device.

A penetration of residual gas of a previous measurement into the respective reaction chamber 46 of the reaction carrier 14 is prevented by the flushing process before the actual measurement.

Figure 12:
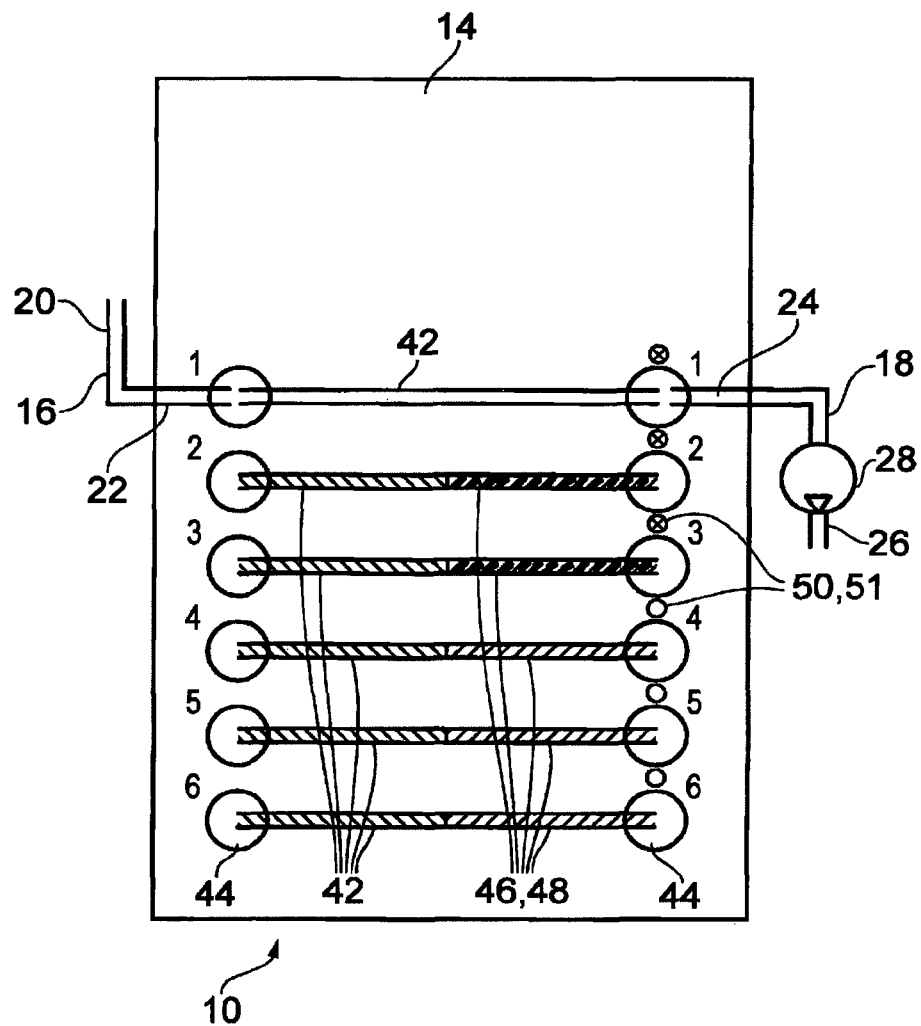
FIG. 12 is a schematic view of a second embodiment of a reaction carrier according to the present invention in a first relative position in the measuring device.
Figure 13:
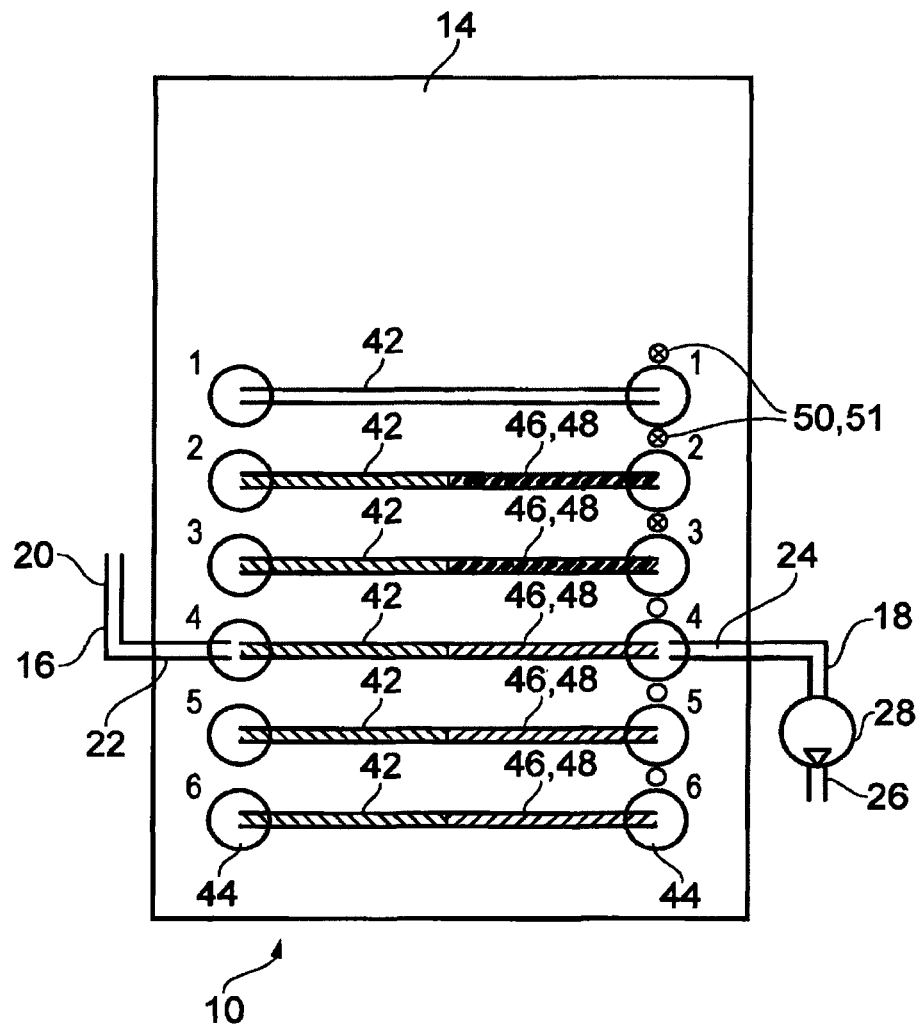
FIG. 13 is a schematic view of the second embodiment of the reaction carrier in a second relative position in the measuring device.

FIGS. 12 and 13 show a schematic view of a measuring system 10 with reaction carrier 14 as well as a schematically shown measuring device 12, of which only the gas ports 22, 24 and the gas inlet and gas outlet channels 16, 18 are shown. The reaction carrier 14 differs from the reaction carrier according to the previous embodiments essentially in that the flow channel 42 foremost in the direction of insertion is designed without a reaction chamber 46. It is especially also possible that this first flow channel 42 has a larger flow cross section, so that a higher volume flow can be delivered through the flow channel 42. The other flow channels 42 of the reaction carrier 40 are designed analogously to the previous embodiments. Reaction chambers 46 already used in previous measurements (flow channels 2 and 3) are shown in dark shading, while unused reaction chambers 46 (flow channels 4 through 6) are shown in light shading. The display pins 50 of the code 51 are correspondingly shown as light and dark, wherein the display pins shown as light correspond to the farther protruding display pins 50 from FIGS. 8 and 9, which code unused reaction chambers 46.

In this embodiment, the measuring method is adapted, so that the reaction carrier 14 for the flushing process is always positioned in the same first relative position, wherein the flushing process is carried out via the flow channel 42 without reaction chamber, which is foremost in the direction of insertion. It is, in principle, also possible that the flow channel 42 without reaction chamber 46 is arranged at a different position of the reaction carrier 14.

Preferably, a checking for leakage flows takes place during each establishing of a connection between the gas ports 22, 24 via a flow channel 42.

In a first step, the gas port 24 of the gas outlet channel 18 is connected to the corresponding connection element 44 of the reaction carrier 14. In a second step, gas is delivered through the gas outlet channel 18 and the flow channel 42 of the reaction carrier 14 connected thereto, wherein the gas flow through the gas outlet channel is measured for the checking of leakage flows. If the system of gas outlet channel and flow channel is gas-tight, then essentially no gas flow through the gas outlet channel 18 is measured, since the flow channel 42 of the reaction carrier 14 is closed in a gas-tight manner via the second connection element 44 closed by the sealing device 62.

In a further step, the gas inlet channel 16 is closed upstream by the valve 54 and the gas port 22 of the gas inlet channel 16 is connected to the corresponding connection element 44 of the reaction carrier 14. Subsequently, gas is delivered by the gas delivery device 28 through the gas outlet channel 18, the flow channel 42 and the gas inlet channel 16, wherein the gas flow through the gas outlet channel is measured for the checking of leakage flows. If the system of gas outlet channel 18, flow channel 42 and gas inlet channel 16 is gas-tight, then essentially no gas flow through the gas outlet channel 18 is measured, since the gas inlet channel 16 is closed in a gas-tight manner by the valve 54.

The measurement of an essentially zero gas flow during the measurement described in the preceding paragraphs in a gas-tight measuring system 10, in which normal pressure is present in the gas outlet channel 18, the flow channel 42 and/or the gas inlet channel 16 before the checking for leakage flows, should be interpreted such that an essentially exponentially decreasing gas flow following the vacuum is measured. In other words, the measured gas flow in a gas-tight measuring system 10 corresponds to the quantity of gas that is present in the channels 16, 18, 42 at the start of the measurement and that is pumped off through the gas delivery device 28 at the time of the checking for leakage flows.

If a leakage flow, i.e., a gas flow exceeding the gas flow mentioned in the preceding paragraph, is measured through the gas outlet channel 18, a corresponding error message is sent by the measuring device 12. The flow channel 42 on the reaction carrier 14 or gas outlet channel 18 and gas inlet channel 16 of the measuring device 12 can then be checked, for example, by the user.

It is also possible that both gas ports 22, 24 of the gas outlet channel 18 and of the gas inlet channel 16 are connected to the corresponding connection elements 44 of the flow channel 42 already in a first step and a single checking for leakage flows is correspondingly performed.

While specific embodiments of the invention have been shown and described in detail to illustrate the application of the principles of the invention, it will be understood that the invention may be embodied otherwise without departing from such principles.

The invention claimed is:

1. A measuring device for measuring a concentration of gaseous and/or aerosol components of a gas mixture for a reaction carrier, which has at least two flow channels, wherein at least one flow channel forms a reaction chamber with a reactant and the reactant is designed to react with at least one component to be measured in the gas mixture in an optically detectable manner, wherein the measuring device comprises:
   a gas inlet channel with a gas port;
   a gas outlet channel with a gas port, wherein the gas ports are designed to establish a gas- and/or aerosol-carrying connection with one of the flow channels of the reaction carrier in order to make possible a flow of the gas mixture from the gas inlet channel through the flow channel to the gas outlet channel;
   a gas delivery device for delivering the gas mixture through the gas outlet channel;
   a reaction carrier delivery device for moving the reaction carrier in relation to the gas inlet channel and the gas outlet channel; and
   a position sensor for detecting a relative position of the reaction carrier and the gas ports, wherein the reaction carrier delivery device is configured
   to position the reaction carrier in a first relative position to the gas ports in a measuring process for establishing a gas- and/or aerosol-carrying connection between the gas ports via a first flow channel for flushing the gas inlet channel, and to position the reaction carrier in a second relative position to the gas ports for establishing a gas- and/or aerosol-carrying connection between the gas ports via a second flow channel, which forms a reaction chamber, for measuring the at least one component of the gas mixture.

2. A measuring device in accordance with claim 1, wherein the reaction carrier delivery device comprises a motor, which makes possible a relative movement of the reaction carrier in at least two opposite directions.

3. A measuring device in accordance with claim 1, further comprising:
   a storage device, which is configured to store data on at least a previous measurement;
   an analysis device configured to decide whether or not a flushing of the gas inlet channel will take place on the basis of the stored data of at least the previous measurement and of the component to be measured in a next measurement.

4. A measuring device in accordance with claim 1, further comprising a valve, which is arranged upstream of the gas inlet channel and which makes possible a gas flow through the gas inlet channel in a first valve position and prevents a gas flow through the gas inlet channel in a second valve position.

5. A reaction carrier for a measuring device comprising a gas inlet channel with a gas port, a gas outlet channel with a gas port, wherein the gas ports are designed to establish a gas- and/or aerosol-carrying connection with the reaction carrier via the gas inlet channel and the gas outlet channel, a gas delivery device for delivering the gas mixture through the gas outlet channel, a reaction carrier delivery device for moving the reaction carrier in relation to the gas inlet channel and the gas outlet channel, and a position sensor for detecting a relative position of the reaction carrier and the gas ports, wherein the reaction carrier delivery device is configured to position the reaction carrier in a first relative position to the gas ports in a measuring process for establishing a gas- and/or aerosol-carrying connection between the gas ports for flushing and to position the reaction carrier in a second relative position to the gas ports for establishing a gas- and/or aerosol-carrying connection between the gas ports for measuring the at least one component of the gas mixture, the reaction carrier comprising:
   at least two flow channels, which extend between two connection elements each, wherein at least one flow channel forms a reaction chamber with a reactant, and the reactant is designed to react with at least one component to be measured in the gas mixture in an optically detectable manner, wherein the connections elements are configured to establish a gas- and/or aerosol-carrying connection with the gas ports of the measuring device in a relative position of the reaction carrier and the measuring device associated with the respective flow channel in order to make possible a flow of the gas mixture from the gas inlet channel through the flow channel to the gas outlet channel; and
   a code configured to be detected by the position sensor of the measuring device and to make possible an independent positioning of the reaction carrier in each of the relative positions associated with the flow channels.

6. A reaction carrier in accordance with claim 5, wherein one of the flow channels is a separate flow channel for flushing the gas inlet channel, wherein the separate flow channel does not form a reaction chamber with a reactant.

7. A measuring method for measuring a concentration of gaseous and/or aerosol components of a gas mixture with
   a reaction carrier, which has at least two flow channels, wherein at least one flow channel a reaction chamber with a reactant, and the reactant is configured to react with at least one component to be measured in the gas mixture in an optically detectable manner, and
   a measuring device with a gas inlet channel and a gas outlet channel, which have each a gas port, the measuring method comprising the steps of:
   positioning the reaction carrier in a first position relative to the gas ports of the measuring device and establishing a gas- and/or aerosol-carrying connection between the gas ports via a first flow channel;
   delivering gas through the gas outlet channel, the first flow channel and the gas inlet channel for flushing the gas inlet channel;
   positioning the reaction carrier in a second position relative to the gas ports of the measuring device and establishing a gas- and/or aerosol-carrying connection between the gas ports via a second flow channel, which has an unused reaction chamber; and
   delivering a gas mixture to be measured through the gas outlet channel, the second flow channel and the gas inlet channel and determining the concentration of the at least one component by means of the optically detectable reaction in the reaction chamber of the second flow channel.

8. A measuring method in accordance with claim 7, wherein the reaction carrier is positioned in the same first relative position for subsequent measurements.

9. A measuring method in accordance with claim 7, further comprising at least one of the steps of:
   deciding, in a certain measurement to be carried out, whether the steps of positioning in the first relative position and of flushing will be carried out, wherein the decision is made as a function of data of the previous measurement and/or data of the measurement to be carried out, wherein the data are based on the component to be measured in the gas mixture and stored in the measuring device and of the measured concentration; and
   establishing the connection between the gas ports in the first relative position via a flow channel with an unused reaction chamber, determining a concentration of the at least one component by means of the optically detectable reaction in the reaction chamber during the delivery of gas for flushing the gas inlet channel and deciding whether a measurement will be carried out at the second relative position with a second flow channel with unused reaction chamber as a function of the concentration determined during the flushing.

10. A measuring method in accordance with claim 7, further comprising the steps of:
   checking for leakage flows before the delivery of gas for flushing the gas inlet channel; wherein at least one of:
   exclusively a gas port of the gas outlet channel is connected to a connection element of the flow channel, and gas is delivered through the gas outlet channel and the flow channel, wherein the gas flow through the gas outlet channel is measured for checking for leakage flows; and
   the gas inlet channel is closed upstream, and both gas ports of the gas outlet channel and of the gas inlet channel are connected to associated connection elements of the flow channel, and gas is delivered through the gas outlet channel, the flow channel and the gas inlet channel, wherein the gas flow through the gas outlet channel is measured for checking for leakage flows.

11. A gas-measuring system for measuring the concentration of gaseous or aerosol components of a gas mixture, the system comprising:
a reaction carrier unit comprising a reaction carrier, flow channels, wherein at least one of the flow channels forms a reaction chamber, and an optically detectable reactant operatively connected to the reaction chamber, the reactant reacting with at least one component to be measured in the gas mixture in an optically detectable manner;
a gas inlet channel with a gas port;
a gas outlet channel with a gas port, wherein the gas ports are configured to establish a fluid connection with one of the flow channels of the reaction carrier in order to make possible a flow of the gas mixture from the gas inlet channel through one of the flow channels to the gas outlet channel;
a gas delivery device for delivering the gas mixture through the gas outlet channel;
a reaction carrier delivery device for moving the reaction carrier in relation to the gas inlet channel and the gas outlet channel; and
a position sensor for detecting a relative position of the reaction carrier and the gas ports and cooperating with the reaction carrier delivery device to position the reaction carrier in a first relative position to the gas ports in a measuring process for establishing a fluid connection between the gas ports via one of the flow channels for flushing the gas inlet channel and to position the reaction carrier in a second relative position to the gas ports for establishing a gas- and/or aerosol-carrying connection between the gas ports via a second flow channel, which forms a reaction chamber, for measuring the at least one component of the gas mixture.

12. A gas-measuring system in accordance with claim 11, further comprising a control unit to control the reaction carrier delivery device based on detected relative position of the reaction carrier and the gas ports received from the position sensor.

13. A gas-measuring system in accordance with claim 12, wherein the reaction carrier unit further comprises a code configured to be detected by the position sensor to make possible an independent positioning of the reaction carrier in each of the plurality of relative positions.

14. A gas-measuring system in accordance with claim 13, wherein the reaction carrier delivery device comprises a motor, which makes possible a relative movement of the reaction carrier in at least two opposite directions.

15. A gas-measuring system in accordance with claim 14, wherein the control unit comprises:
a storage device configured to store data on at least a previous measurement; and
an analysis device configured to decide whether or not a flushing of the gas inlet channel will take place on the basis of the stored data of at least the previous measurement and data of the component to be measured in a next measurement.

16. A gas-measuring system in accordance with claim 15, further comprising a valve arranged upstream of the gas inlet channel and providing a first valve position which makes possible a gas flow through the gas inlet channel and a second valve position that prevents a gas flow through the gas inlet channel.

17. A gas-measuring system in accordance with claim 15, wherein at least one of the flow channels is a separate flow channel for flushing the gas inlet channel, wherein the separate flow channel does not form a reaction chamber with a reactant.

* * * * *